United States Patent [19]
Nakai et al.

[11] Patent Number: 5,332,754
[45] Date of Patent: * Jul. 26, 1994

[54] NAPHTHYLOXAZOLIDONE DERIVATIVES

[75] Inventors: Hideo Nakai, Takarazuka; Koichiro Yamada, Saitama; Sumihiro Nomura, Misato; Mamoru Matsumoto, Nara; Hiroshi Iwata, Osaka, all of Japan

[73] Assignee: Tanabe Seiyaku Co., Ltd., Osaka, Japan

[*] Notice: The portion of the term of this patent subsequent to Jan. 26, 2010 has been disclaimed.

[21] Appl. No.: 961,873

[22] Filed: Oct. 15, 1992

Related U.S. Application Data

[63] Continuation of Ser. No. 599,564, Oct. 18, 1990, Pat. No. 5,182,296.

[30] Foreign Application Priority Data

Oct. 26, 1989 [JP] Japan ................. 1-279305

[51] Int. Cl.$^5$ ............................ A61K 31/42
[52] U.S. Cl. .................... 514/376; 548/231; 548/232
[58] Field of Search ............ 548/231, 232; 514/376

[56] References Cited

U.S. PATENT DOCUMENTS

| | | | |
|---|---|---|---|
| 3,654,298 | 4/1972 | Douzon et al. | 548/231 |
| 3,655,687 | 4/1972 | Fauran et al. | 548/232 |
| 4,150,029 | 4/1979 | Dostert et al. | 548/231 |
| 4,348,393 | 9/1982 | Bourgery et al. | 514/376 |
| 4,517,197 | 5/1985 | Ancher et al. | 548/231 |
| 4,985,429 | 1/1991 | Wang et al. | 514/376 |
| 5,164,510 | 11/1992 | Brickner et al. | 548/231 |
| 5,182,296 | 1/1993 | Nakai et al. | 514/376 |

FOREIGN PATENT DOCUMENTS

| | | |
|---|---|---|
| 2832632 | 2/1979 | Fed. Rep. of Germany . |
| 1530783 | 5/1968 | France . |
| 1602544 | 12/1970 | France . |
| 8108544 | 11/1981 | France . |
| 372056 | 9/1963 | Switzerland . |
| 382167 | 11/1964 | Switzerland . |
| 753987 | 8/1956 | United Kingdom . |
| 2072663 | 10/1981 | United Kingdom . |

OTHER PUBLICATIONS

Iwakura et al., "Synthesis 3,5-unsunstituted 2-oxazolidone derivative by the reaction between N-arylurethane and substituted phenyl glycidyl ethers," *Chemical Abstracts* 64(6), Abstract No. 8163a, Mar. 14, 1966.

(List continued on next page.)

*Primary Examiner*—Donald G. Daus
*Attorney, Agent, or Firm*—Browdy and Neimark

[57] ABSTRACT

A naphthyloxazolidone derivative of the formula:

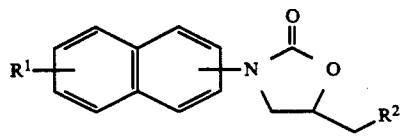

wherein $R^1$ is hydrogen atom, hydroxy group, nitro group, amino group, sulfo group, aminosulfonyl group, a lower alkenyloxy group, a lower alkynyloxy group, a mono or di(lower alkyl)aminocarbonyloxy group, a lower alkanoyloxy group or a lower alkoxy group which may have a substituent selected from an aryl group, a cycloalkyl group, an oxygen-containing heteromonocyclic group, hydroxy group, a lower alkoxy group, cyano group, a di(lower alkyl)amino group, aminocarbonyl group, a lower alkoxycarbonyl group, a lower alkanoyloxy group, a lower alkylthio group, a lower alkylsulfinyl group and a lower alkylsulfonyl group; $R^2$ is hydroxy group, a lower alkoxy group, a lower alkylsulfonyloxy group, triazo group or an amino group which may have a substituent selected from a lower alkyl group and a lower alkanoyl group, and a pharmaceutically acceptable salt thereof are disclosed. Said derivative and a pharmaceutically acceptable salt thereof are useful as an antidepressant.

11 Claims, No Drawings

OTHER PUBLICATIONS

Synthesis, Apr. 1979, pp. 277–279, Georg Thieme Publishers, Stuttgart, Germany; H. Ulrich et al., "Synthesis and reactions of isocyanatophenols and isocyanatonaphtols".

Tetrahydron, vol. 43, No. 11, 1987, pp. 2505–2512, Pergamon Journals Ltd. Oxford, GB; G. Cardillo et al., "An efficient synthesis of (R)-(+)- and (S)-(−)-propranolol from resolved 5-iodomethyloxazo-lidin-2-ones".

Chemical Abstracts, vol. 98, No. 9, Feb. 28, 1983, p. 593, abstract No. 71723x, Columbus, Ohio, USA.

Chemical Abstracts, vol. 71, No. 7, Aug. 18, 1969, p. 200, abstract no. 29515y, Columbus, Ohio, USA; T. Takematsu et al.: "Reaction of chemical structure to herbicidal activity and properties of carbamates".

Jones, J. I. et al., "The Reaction of Carbonyl Chloride with 1:2-Expoxides", *J. Chem. Soc.*, (1957), pp. 2735–2743 [C.A. 1635–43d (1957)].

*Chemical Abstracts*, 71:91460e (1969); 75:63762u (1971); 78:58392f (1973); and 79:78663u (1973), Douzon et al.

*Chemical Abstracts*, 103:160009h (1985), Douzon, C. et al.; Beilsteins Handbuch, 145, 4, Aufl. XXVII.

NAPHTHYLOXAZOLIDONE DERIVATIVES

CROSS-REFERENCE TO RELATED APPLICATIONS

This is a continuation of application Ser. No. 07/599,564, filed Oct. 18, 1990, now U.S. Pat. No. 5,182,296.

This invention relates to novel naphthyloxazolidone derivatives which are useful as an antidepressant and processes for preparing the same.

Monoamine oxidase (MAO), which catalyzes oxidative deamination of monoamines to produce aldehydes, is classified into two groups (i.e., MAO-A and MAO-B) according to its substrate specificity. MAO-A catalyzes oxidative deamination of neurotransmitters such as serotonin, noradrenaline and the like, whereas MAO-B catalyzes oxidative deamination of phenethylamine, and the like.

Known MAO inhibitors which have been used as an antidepressant have no selective inhibitory activity against MAO-A or MAO-B and show irreversible and long-lasting inhibitory activity. Therefore, the known MAO inhibitors are disadvantageous in that they have side effects such as hepatic injuries, migraine and hypertensive crises after the ingestion of tyramine-containing food i.e., cheese effect.

An object of the present invention is to provide novel naphthyloxazolidone derivatives which have potent reversible and selective inhibitory activity against MAO-A and are useful as an antidepressant.

Another object of the present invention is to provide processes for preparing said naphthyloxazolidone derivatives.

Another object of the present invention is to provide novel intermediates of said naphthyloxazolidone derivatives.

The present invention relates to a naphthyloxazolidone derivative of the formula:

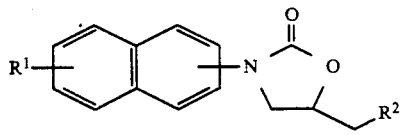

wherein $R^1$ is hydrogen atom, hydroxy group, nitro group, amino group, sulfo group, aminosulfonyl group, a lower alkenyloxy group, a lower alkynyloxy group, a mono or di(lower alkyl)aminocarbonyloxy group, a lower alkanoyloxy group or a lower alkoxy group which may have a substituent selected from an aryl group, a cycloalkyl group, an oxygen-containing heteromonocyclic group, hydroxy group, a lower alkoxy group, cyano group, a di(lower alkyl)amino group, aminocarbonyl group, a lower alkoxycarbonyl group, a lower alkanoyloxy group, a lower alkylthio group, a lower alkylsulfinyl group and a lower alkylsulfonyl group; $R^2$ is hydroxy group, a lower alkoxy group, a lower alkylsulfonyloxy group, triazo group or an amino group which may have a substituent selected from a lower alkyl group and a lower alkanoyl group, or a pharmaceutically acceptable salt thereof.

Examples of the naphthyloxazolidone derivative (I) of the present invention include those of the formula (i) in which an aryl group is phenyl group, a cycloalkyl group is a cycloalkyl group of 3 to 6 carbon atoms, and an oxygen-containing heteromonocyclic group is a tetrahydrofuryl group. Among them, preferred compounds include those of the formula (I) in which $R^1$ is a lower alkenyloxy group, a lower alkanoyloxy group or a lower alkoxy group which may have a substituent selected from cyclopropyl group, hydroxy group and cyano group; $R^2$ is a lower alkoxy group. More preferred compounds are those of the formula (I) in which $R^1$ is a lower alkoxy group which may have a substituent selected from cyclopropyl group and cyano group. Another preferred compounds are those of the formula (I) in which $R^1$ is at the 6-position of naphthalene ring and the 5-substituted-2-oxazolidon-3-yl group is at the 2-position of naphthalene ring.

According to the present invention, the naphthyloxazolidone derivatives (I) can be prepared either by

[A] reacting a lower alkyl naphthylcarbamate compound of the formula:

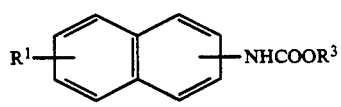

wherein $R^3$ is a lower alkyl group and $R^1$ is the same as defined above, or a salt thereof with an oxirane compound of the formula:

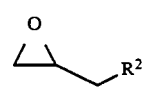

wherein $R^2$ is the same as defined above, or a salt thereof, or by

[B] reacting a naphthalene compound of the formula:

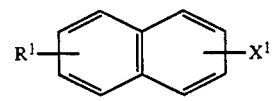

wherein $X^1$ is a reactive residue, $R^1$ is the same as defined above, or a salt thereof with a 2-oxazolidone compound of the formula:

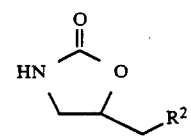

wherein $R^2$ is the same as defined above, or a salt thereof.

The naphthyloxazolidone derivative of the formula:

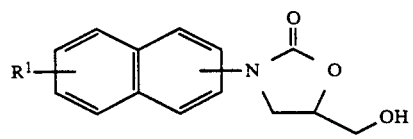

wherein $R^1$ is the same as defined above, can also be prepared by

[C] condensing a propanediol compound of the formula:

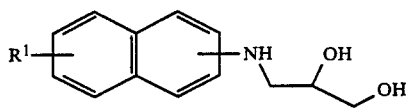

wherein R¹ is the same as defined above, or a salt thereof with a carbonyl compound of the formula:

 (VII)

wherein X² is a reactive residue.

The naphthyloxazolidone derivative of the formula:

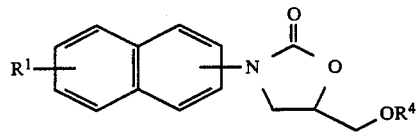 (I-b)

wherein R⁴ is a lower alkyl group or a lower alkylsulfonyl group, and R¹ is the same as defined above, can also be prepared by

[D] condensing the compound (I-a) with the compound of the formula:

 (VIII)

wherein X³ is a reactive residue and R⁴ is the same as defined above.

The naphthyloxazolidone derivative of the formula:

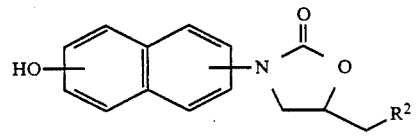 (I-c)

wherein R² is the same as defined above, can also be prepared by

[E] reducing the compound of the formula:

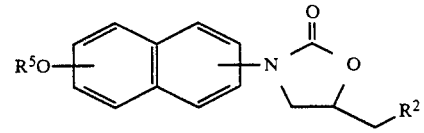 (I-d)

wherein R⁵ is an aryl-lower alkyl group, R² is the same as defined above, or a salt thereof.

Further, the naphthyloxazolidone derivative of the formula:

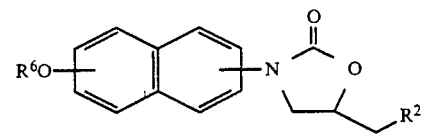 (I-e)

wherein R⁶ is a lower alkenyl group, a lower alkynyl group, a mono or di(lower alkyl)aminocarbonyl group, a lower alkanoyl group or a lower alkyl group which may have a substituent selected from an aryl group, a cycloalkyl group, an oxygen-containing heteromonocyclic group, hydroxy group, a lower alkoxy group, cyano group, a di(lower alkyl)amino group, aminocarbonyl group, a lower alkoxycarbonyl group, a lower alkanoyloxy group, a lower alkylthio group, a lower alkylsulfinyl group and a lower alkylsulfonyl group, R² is the same as defined above, can also be prepared by

[F] condensing the compound (I-c) or a salt thereof with a compound of the formula:

$$R^6\text{-}X^4 \quad (IX)$$

wherein X⁴ is a reactive residue, R⁶ is the same as defined above, or a salt thereof.

Among the naphthyloxazolidone derivative (I-e), a compound of the formula:

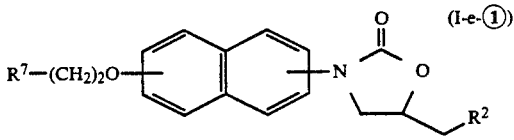 (I-e-①)

wherein R⁷ is cyano group or a lower alkoxycarbonyl group, and R² is the same as defined above, can also be prepared by

[G] reacting a compound (I-c) or a salt thereof with a compound of the formula:

$$R^7\text{-CH=CH}_2 \quad (X)$$

wherein R⁷ is the same as defined above.

Further, among the naphthyloxazolidone derivative (I-e), a compound of the formula;

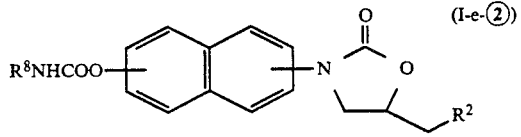 (I-e-②)

wherein R⁸ is a lower alkyl group, and R² is the same as defined above, can also be prepared by

[H] reacting the compound (I-c) or a salt thereof with a lower alkyl isocyanate.

The reaction of the compound (II) with the compound (III) (i.e., Step [A]) can be carried out in the presence of a base. Any conventional base may be used for this reaction. Preferred examples of the base include a tri(lower alkyl)amine, a 4-di(lower alkyl)aminopyridine, an alkali matal hydroxide, an alkali metal alkoxide and the like. The reaction may be carried out in the presence or absence of a solvent such as dimethylformanide, dimethylacetamide, dimethylsulfoxide, xylene or the like. It is preferred to carry out the reaction under heating, for example, at a temperature between 50° and 150° C., preferably at a temperature between 90° and 110° C.

The reaction of the compound (IV) with the compound (V) (i.e., Step [B]) can be carried out in the presence of an acid acceptor. Examples of the acid acceptor include conventional organic or inorganic bases such as an alkali metal bicarbonate, an alkali metal carbonate, an alkali metal hydride, a tri(lower alkyl)amine and so forth. Examples of the reactive residue (X¹) of the compound (IV) include a conventional reactive residue such as a halogen atom and the like. The reaction may be carried out in the presence or absence of a solvent such as dimethylformanide, dimethylacetamide, dimethylsulfoxide, xylene or the like. It is preferred to carry out the reaction under heating, for example, at a temperature between 150° and 220° C. In particular, said reaction preferably proceeds by adding copper power to the reaction system.

The condensation reaction of the compound (VI) with the compound (VII) (i.e., Step [C]) can be carried out in the presence of a base. The same bases as mentional in Step [A] are preferably used for the reaction. Examples of the reactive residue ($X^2$) of the compound (VII) include an lower alkoxy group, imidazolyl group, halogen atom and the like. It is preferred to carry out the reaction in a solvent such as toluene, xylene, methylene chloride, chloroform, tetrahydrofuran and so forth and at room temperature or under heating, for example, at a temperature between 10° and 150° C.

The condensation reaction of the compound (I-a) with the compound (VIII) (i.e., Step [D]) can be carried out in the presence or absence of an acid acceptor. The same bases as mentioned in Step [B] are preferably used for the reaction as the acid acceptor. Examples of the reactive residue ($X^3$) of the compound (VIII) include a halogen atom, a lower alkanoyloxy group, a (lower alkyl) sulfonyloxy group, arylsulfonyloxy group and the like. It is preferred to carry out the reaction in a solvent such as acetone, ethyl acetate, N,N-dimethylformamide, tetrahydrofuran, methylene chloride, diethyl ether, dioxane or the like. Said reaction preferably proceeds at room temperature or under heating, for example, at a temperature between 30° and 120° C.

The reduction of the compound (I-d) (i.e., Step [E]) can be conducted in a conventional manner. For example, said reduction is carried out by subjecting the compound (I-d) to catalytic hydrogenation in the presence of palladium-carbon, Raney nickel, Raney cobalt, platinum, rhodium, or the like. The catalytic hydrogenation preferably proceeds in a solvent such as tetrahydrofuran, dioxane, a lower alkanol or the like, under atmospheric pressure or increased pressure and at room temperature or under warming, for example, at a temperature between 10° and 50° C.

The condensation reaction of compound (I-c) with the compound (IX) (i.e., Step [F]) can be carried out in the presence or absence of an acid acceptor. The same organic or inorganic bases as mentioned in Step [B] are prefelably used for the reaction as the acid acceptor. Examples of the reactive residue ($X^4$) includes the same as the reactive residue ($X^3$). It is preferred to carry out the reaction in a solvent such as acetone, ethyl acetate, dimethylformamide, dimethylsulfoxide or the like and at room temperature or heating, for example, at a temperature between 30° and 120° C.

The reaction of the compound (I-c) with the compound (X) (i.e., Step [G]) and the reaction of the compound (I-c) with the lower alkyl isocyanate (i.e., Step [H]) can be carried out in the presence of a base. The same bases as mentioned in Step [A] are prefelably used for the reaction, and in addition, benzyltri(lower alkyl)ammonium hydroxide, tetra(lower alkyl)ammonium hydroxide and the like can also be used. The reaction preferably proceeds in a solvent such as tetrahydrofuran, methylene chloride, dimethylformamide, dimethylsulfoxide or the like and at room temperature or under heating, for example, at a temperature between 20° and 80° C.

In the above-mentioned reactions, the starting compounds of the present invention may be used either in a free form or in the form of a salt. For example, the compounds (VI), (I-a) and (I-c), and the compounds (II) to (V), (IX) and (I-d) which have hydroxy group are, if required, used in the form of an alkali metal salt, an alkali earth metal salt, an ammonium salt and the like. On tile other hand, the compounds (V) and (VI), and the compounds (II) to (IV), (IX), (I-a), (I-c) and (I-d) which have amino group or mono or di(lower alkyl)amino group are, if required, used in the form of an organic or inorganic acid addition salt.

Concomitantly, some of the naphthyloxazolidone derivative (I) of the present invention can, if required, be converted into another naphthyloxazolidone derivative (I) in a conventional manner. For example, when $R^1$ is nitro group and/or $R^2$ is triazo group, said group(s) may be converted into amino group(s) by catalytic hydrogenation. If required, the resulting amino group(s) may be converted into a lower alkanoylamino group(s), or may be converted into hydroxy group(s) or a lower alkoxy group(s) after diazotization of said amino group(s). When $R^1$ is sulfo group, said group may be converted into aminosulfo group by a conventional amination. Further, when $R^1$ is a (lower alkyl)thio-substituted-lower alkoxy group, said group may be converted into a (lower alkyl)sulfinyl-substituted-lower alkoxy group or a (lower alkyl)sulfonyl-substituted-lower alkoxy group by oxidation thereof. On the other hand, when $R^2$ is a lower alkoxy group, said group may be converted into hydroxy group by hydrolysis thereof, and if required, be converted into a lower alkylsulfonyloxy group in a conventional manner, and if necessary, further converted into a lower alkylamino group or a triazo group.

The naphthyloxazolidone derivatives (I) of the present invention include within its scope either one of optically active isomers and the mixtures thereof. Since the reactions of the present invention as mentioned above proceed without accompanying racemization, tile compound (I) can be obtained as an optically active compound by using an optically active starting materials.

Further, when the naphthyloxazolidone derivative (I) is in form of a racemic modification, it can be separated into each of two optically active isomers thereof in a conventional manner, for example, by the steps of:
(1) treating said compound (I) with an alkali metal hydroxide (e.g., potassium hydroxide).
(2) protecting the amino group of the resultant compound with a lower alkoxycarbonyl group.
(3) reacting the resultant compound with an optically active 1-(2-naphthylsulfonyl)pyrrolidin-2-carbonyl chloride,
(4) separating each of two kinds of resulting diastereomers by taking advantage of difference in solubilities thereof or column chromatography,
(5) hydrolyzing each of the diastereomers with an alkali metal hydroxide (e.g., sodium hydroxide), and then,
(6) reacting the resultant compound with compound (VII) in the same manner as described in Step [C].

The naphthyloxazolidone derivatives (I) can be used for pharmaceutical use either in a free Form or in the form of a pharmaceutically acceptable salt. Examples of the pharmaceutically acceptable salts include salts with an organic or inorganic base such as alkali metal salts (e.g., sodium salt, potassium salt), alkaline earth metal salts (e.g., calcium salt, magnesium salt), ammonium salt and the like, and organic or inorganic acid addtion salts such as hydrochloride, sulfate, acetate, benzensulfonate and the like.

The naphthyloxazolidone derivative (I) or a pharmaceutically acceptable salt thereof has excellent reversible and selective MAO-A inhibitory activity. Accordingly, the compound (I) or a pharmaceutically acceptable salt thereof is useful as a therapeutic or prophylactic agent for depressive conditions such as depression, senile depression, abulia, axiety, insomnia, anorexia and the like in warm-blood animals including human beings. In particular, the compound (I) or a pharmaceutically acceptable salt thereof is characterized in that it shows short duration of inhibitory activity and has no side effect such as hepatic injuries, migraine, cheese effect or the like. Moreover, the compound (I) or a pharmaceutically acceptable salt thereof is low in toxicity and have high safety as a pharmaceuticals. For example, when 3-(6-cyanoethoxy-2-naphthyl)-5-methoxymethyl-2-oxazolidone was administered orally to mice at a dose of 2g/kg, no mice died during 2 week-observation period.

The naphthyloxazolidone derivative (I) or a pharmaceutically acceptable salt thereof may be administered either orally or parenterally. They may also be used in the form of pharmaceutical preparations such as tablets, capsules, powders, granules, injections and the like, if necessary, in admixture with a pharmaceutically acceptable carrier, diluent or disintegrant.

The dose of the naphthyloxazolidone derivative (I) or a pharmaceutically acceptable salt thereof may vary depending on the age, body weight and condition of patients, the kind and severity of diseases to be treated, administration route, etc. but it may usually be in the range of about 0.01 to about 250 mg per kg, preferably about 0.1 to about 30 mg per kg, per day.

Among the starting compounds of the present invention, the compounds (II), (V) and (VI) are novel. The compound (II) may be prepared, for example, by reacting a naphthylamine compound of the formula:

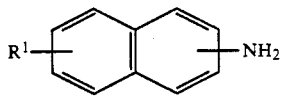
(XI)

wherein $R^1$ is the same as defined above, with a compound of the formula:

$$X^5\text{-COOR}^3 \quad (XII)$$

wherein $X^5$ is halogen atom and $R^3$ is the same as defined above in the presence of an acid acceptor (e.g., sodium bicarbonate) and in a solvent (e.g., methylene chloride). The compound (V) may be prepared, for example, by reacting an aminopropanol compound of the formula:

(XIII)

wherein $R^2$ is the same as defined above, with a benzyloxycarbonyl halide or a lower alkoxy-carbonyl halide in the presence of an acid acceptor (e.g., triethylamine) and in a solvent (e.g., tetrahydrofuran), and then, subjectng the resultant compound to intermolecular cyclization in the presence of a base (e.g., sodium hydride). Furthermore, the compound (VI) may be prepared, for example, by reacting the naphthylamine compound (XI) with 2,2-dimethyl-4-tosyloxy-1,3-dioxolane, and then, hydrolyzing the resultant compound in the presence of an acid (e.g., hydrochloric acid).

In this specification and Claims, the terms "a lower alkyl group", "a lower alkoxy group", "a lower alkanoyl group", "a lower alkenyl group" and "a lower alkynyl group" represent an alkyl group of one to 6 carbon atoms, an alkoxy group of one to 6 carbon atoms, an alkanoyl group of 2 to 6 carbon atoms, an alkenyl group of 2 to 6 carbon atoms and an alkynyl group of 2 to 6 carbon atoms, respectively.

EXPERIMENT 1

Inhibitory effect against MAO-A activity of cerebral mitochondorian fraction from rat (in vitro)

(Method)

A suspension (7mg protein/ml) of mitochondorial fraction obtained from cerebral tissue of rats in a conventional manner was used as a sample of enzyme, and serotonin was used as the substrate. of MAO-A. The MAO-A activity was estimated in terms of the amount of ammonia produced from serotonin by the enzymatic reaction.

Inhibitory rate of the test compounds ($10^{-7}$ M) against the MAO-A activity was calculated according to the following equation.

$$\text{Inhibitory rate (\%)} = \left[1 - \frac{NH_3(T)}{NH_3(C)}\right] \times 100$$

$NH_3(T)$: the amount of $NH_3$ in test tube (addtion of test compound) $NH_3(C)$: the amount of $NH_3$ in control tube (no addition of test compound)

(Results)

The results are shown in the following Table 1.

TABLE 1

| $R^1$ | Inhibitory rate (%) against MAO-A activity |
|---|---|
| —H | 78.4 |
| —OCH(CH$_3$)$_2$ | 98.8 |
| —O(CH$_2$)$_2$CN | 98.1 |
| —O(CH$_2$)$_3$CN | 95.5 |
| —OCH$_2$—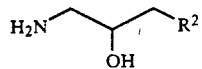 | 93.5 |
| —O(CH$_2$)$_3$OH | 91.7 |
| —OCH$_2$CH=CH$_2$ | 96.8 |
| —OCOCH$_3$ | 76.6 |

EXPERIMENT 2

Inhibitory effect against cerebral MAO-A and MAO-B activity in mouse.

(Method)

A test compound (30 mg/kg) suspended in 0.5% aqueous sodium carboxymethylcellulose (CMC-Na) solution was administered orally to a group of 3 mice. The brain was excised 45 minutes after the administration. A control group was administered with the 0.5% aqueous CMC-Na solution alone.

The brain tissue was homogenized in 9 volumes of ice-cold distilled water and the homogenate was used as enzyme. MAO-A activity was estimated in the same manner as described in Experiment 1, whereas MAO-B activity was estimated in terms of the amount of benzaldehyde formed from benzylamine according to the method as described in "The Journal of Laboratory and Clinical Medicine, vol. 62, P.P. 766–776 (1963)".

Inhibitory rate of the test compound against the MAO-B activity are calculated according to the following equation.

$$\text{Inhibitory rate (\%)} = \left[1 - \frac{BA(T)}{BA(C)}\right] \times 100$$

BA(T): the amount of benzaldehyde in the medicated group
BA(C): the amount of benzaldehyde in the non-medicated control group (Results)

The results are shown in the following Table 2.

TABLE 2

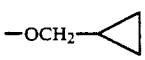

| R1 | Inhibitory rate (%) | |
|---|---|---|
|  | MAO-A | MAO-B |
| —OCH(CH$_3$)$_2$ | 86.8 ± 5.4 | 3.6 ± 5.3 |
| —O(CH$_2$)$_2$CN | 109.2 ± 3.5 | −1.0 ± 2.3 |
| —O(CH$_2$)$_3$CN | 99.8 ± 16.1 | −1.9 ± 4.8 |
| —OCH$_2$—◁ | 71.4 ± 4.3 | −4.5 ± 5.9 |
| —O(CH$_2$)$_3$OH | 57.1 ± 4.3 | 1.0 ± 0.8 |
| —OCOCH$_3$ | 56.4 ± 7.4 | −3.1 ± 1.8 |
| (positive control) pargyline | 42.0 ± 2.4 | 98.3 ± 5.9 |

EXAMPLE 1

(1) A mixture of 16.7 g of ethoxycarbonyl chloride and 20 ml of methylene chloride is added dropwise to a mixture of 20.0 g of 2-naphthylamine, 17.6 g of sodium bicarbonate, 100 ml of water and 200 ml of methylene chloride under ice-cooling and stirring. The mixture is stirred overnight at room temperature. Chloroform is added to the mixture and the organic layer is separated, dried and treated with charcol. The residue is recrystallized from ethyl acetate-hexane to give 25.26 g of N-ethoxycarbonyl-2-naphthylamine.
m.p. 69.0°–70.5° C.

(2) A mixture of 3.82 g of the product obtained in the the paragraph (1), 3.13 g of 2-(methoxymethyl)oxirane and 0.4 g of triethylamine is refluxed for 3.5 hours. The reaction mixture is extracted with ethyl acetate. The extract is washed with water, dried and filtered. The filtrate is condensed and the residue is purified by silica gel column chromatography [solvent: ethyl acetate - hexane (2:3)] to give 3.75 g of crude 5-methoxymethyl-3-(2-naphthyl)-2-oxazolidone. The recrystallization of this crude product from ethyl acetate - hexane gives 3.17 g of colorless needles.
m.p. 79.5°–81.5° C., EXAMPLE 2 to 5

(2) The corresponding starting compounds are treated in the same manner as described in Example 1-(1) to give compounds shown in Table 3.

TABLE 3

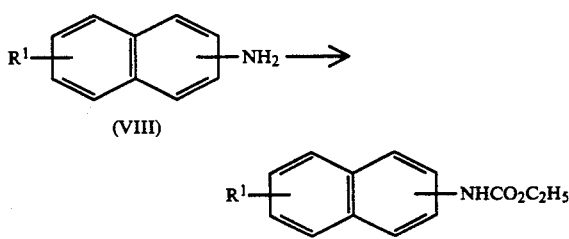

| | | Compound (II-a) | |
|---|---|---|---|
| Ex. No. | R$^1$ | position* | Physical Properties |
| 2-(1) | 7-NO$_2$ | 2 | m.p. 143–144° C. (ethyl acetate - hexane) |
| 3-(1) | 5-OH | 2 | m.p. 117–121° C. (ethyl acetate - isopropyl ether - hexane) |
| 4-(1) | 6-SO$_3$Na | 2 | m.p. >320° C. (isopropyl ether - water) IR$_{Max}^{Nujol}$ (cm$^{-1}$): 3270, 1700 |
| 5-(1) | —H | 1 | m.p. 80.5–81° C. (ethyl acetate - hexane) |

*A position of —NHCO$_2$C$_2$H$_5$ in naphthalene ring (2) The products obtained in the paragraph (1) are treated in the same manner as described in Example 1-(2) to give compounds shown in Table 4.

TABLE 4

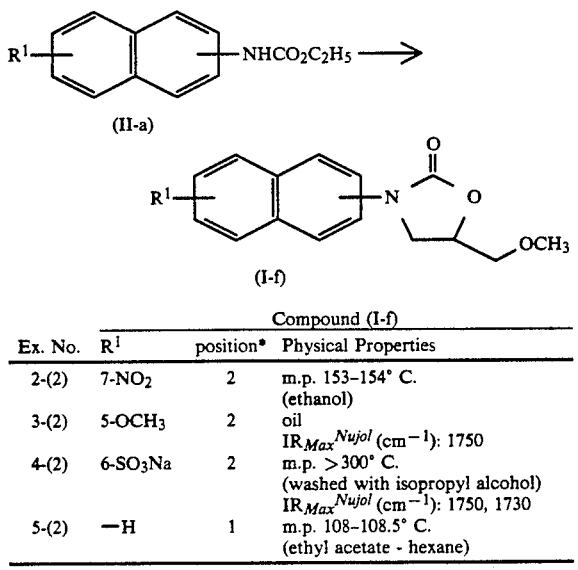

*A position of 5-methoxymethyl-2-oxazolidon-3-yl group in naphthalene ring

| Ex. No. | R¹ | position* | Physical Properties |
|---|---|---|---|
| 2-(2) | 7-NO$_2$ | 2 | m.p. 153–154° C. (ethanol) |
| 3-(2) | 5-OCH$_3$ | 2 | oil IR$_{Max}^{Nujol}$ (cm$^{-1}$): 1750 |
| 4-(2) | 6-SO$_3$Na | 2 | m.p. >300° C. (washed with isopropyl alcohol) IR$_{Max}^{Nujol}$ (cm$^{-1}$): 1750, 1730 |
| 5-(2) | —H | 1 | m.p. 108–108.5° C. (ethyl acetate - hexane) |

EXAMPLE 6

A mixture of 4.63 g of N-ethoxycarbonyl-2-naphthylamine, 4.2 g of 2-(butoxymethyl)oxirane and 0.22 g of triethylamine is stirred at 100° to 105° C. for 1.5 hours. The reaction mixture is cooled, and the crystalline precipitates are collected by filtration, treated with charcol and recrystallized from ethyl acetate - isopropyl ether - hexane. 4.7 g of 3-(2-naphthyl)-5-tert.butoxymethyl-2-oxazolidone are obtained.
m.p. 112.5°–113.0° C.

EXAMPLE 7

(1) 19.69 g of triethylamine are added to a solution of 10.23 g of 1-amino-3- methoxy-2-propanol in 100 ml of tetrahydrofuran. After the mixture is cooled, a solution of 16.60 g of benzyloxycarbonyl chloride in 50 ml of tetrahydrofuran is added dropwise thereto for 30 minutes. The mixture is stirred at room temperature for one hour. The reaction mixture is diluted with ethyl acetate, washed with water and dried. The residue is purified by silica gel column chromatography [solvent: ethyl acetate - hexane (2:1)]. 13.2 g of 1-benzyloxycarbonylamino-3- methoxy-2-propanol are obtained as colorless oil.

IR$_{Max}^{Neat}$(cm$^{-1}$): 3340(br), 1700.

(2) 10.2 g of the product obtained in the paragraph (1) are dissolved in 200 ml of tetrahydrofuran, and 1.624 g of sodium hydride (60% dispersion in oil) are added thereto. The mixture is stirred at room temperature for one hour. Water is added to the reaction mixture and the mixture is extracted with chloroform. The extract is condensed and the residue is purified by silica gel column chromatography [solvent: ethyl acetate - hexane (3:1)]. 3.36 g of 5-methoxymethyl-2-oxazolidone are obtained as colorless oil.

IR$_{Max}^{Neat}$(cm$^{-1}$): 3320(br), 1650.

(3) 1.2 g of sodium methoxide are added to a mixture of 38.44 g of 1-amino-3-methoxy-2-propanol and 64.78 g of diethyl carbonate. The mixture is stirred at 100° C. for 2.5 days. An excess diethyl carbonate is removed from the mixture. The residue is dissolved in 50 ml of anhydrous tetrahydrofuran, and 1.4 g of 63% of sodium hydride are added thereto. The mixture is stirred overnight at room temperature. 4 ml of acetic acid are added to the reaction mixture, and the mixture is stirred at room temperature for 3 hours. Insoluble materials are filtered off. The filtrate is condenced and the residue is distilled under reduced pressure. 42.38 g of 5-methoxymethyl-2-oxazolidone are obtained as colorless oil.

The physico-chemical properties of this product are identical to those of the compound obtained in the paragraph (2).

(4) 6.10 g of activated copper powder and 2.76 g of sodium carbonate are added to a mixture of 5.24 g of the product obtained in the paragraph (2) or (3) and 4.14 g of 2-bromonaphthalene. The mixture is stirred at 200° C. for 3 hours. After the mixture is cooled, ethyl acetate is added thereto and insoluble materials are filtered off. The filtrate is evaporated under reduced pressure to remove the solvent. The residue is purified by silica gel column chromatography [solvent: ethyl acetate - hexane (2:3)]. 2.36 g of 5-methoxymethyl-3-(2-naphthyl)-2-oxazolidone are obtained as colorless needles.

The physico-chemical properties of this product are identical to those of the compound obtained in Example 1.

EXAMPLES 8 and 9

The corresponding starting compounds are treated in the same manner as described in Example 7-(4) to give the compounds shown in Table 5.

TABLE 5

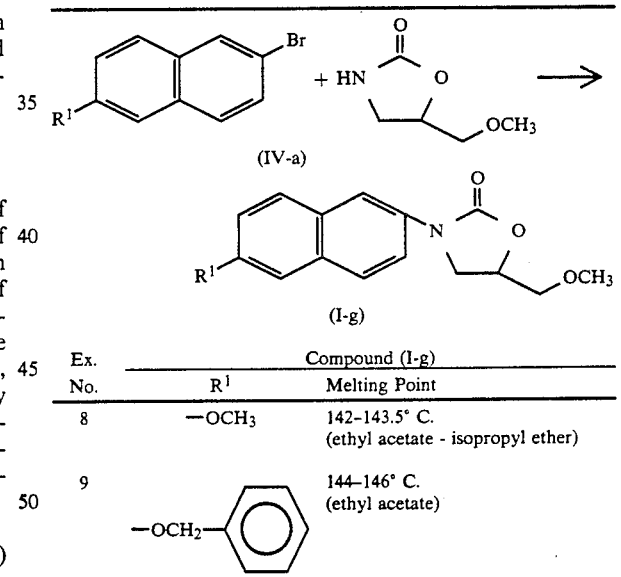

| Ex. No. | R¹ | Melting Point |
|---|---|---|
| 8 | —OCH$_3$ | 142–143.5° C. (ethyl acetate - isopropyl ether) |
| 9 | —OCH$_2$—⟨phenyl⟩ | 144–146° C. (ethyl acetate) |

EXAMPLE 10

(1) 100 g of 1,2-epoxypropyl tert.-butyl ether are added dropwise to 500 ml of conc. aqueous ammonia under ice-cooling and tile mixture is stirred at room temperature for 20 hours. The reaction mixture is evaporated under reduced pressure to remove the aqueous ammonia. Chloroform is added to the residue. The mixture is dried with potassium carbonate. Insoluble materials are filtered off and the filtrate is evaporated to remove the solvent. The residue is distilled under reduced pressure. 49.3 g of 1-amino-3-tert.-butoxy-2-propanol are obtained.

b.p. 109°–110° C./8 mmHg;

m.p. 41°-43° C.

(2) A mixture of 49.3 g of the product obtained in the paragraph (1), 4.9 l of diethyl carbonate and 0.18 g of sodium methoxide is heated at 50° C. for 3 hours. About 40 ml of ethanol which is produced during the reaction are evaporated. After the reaction is completed, the mixture is evaporated under reduced pressure to remove excess diethyl carbonate. The residue is cooled, and the crystalline precipitates are washed with hexane. 55.4 g of 5-tert.-butoxymethyl-2-oxazolidone are obtained as colorless crystals.

m.p. 57°-65° C.

(3) 1.1 g of the product obtained in the paragraph (2) and 1.0 g of 2-benzyloxy-6-bromonaphthalene are treated in the same manner as described in Example 7-(4). 0.73 g of 3-(6-benzyloxy-2-naphthyl)-5-tert.-butoxymethyl-2-oxazolidone is obtained as colorless crystals.

m.p. 151.5°-152° C. (ethyl acetate - isopropyl ether).

EXAMPLE 11

(1) 21.0 g of tosyl chloride are added portionwise to a mixture of 14.4 g of (R)-α,β-isopropylidene glycerol and 60 ml of pyridine under ice-cooling. The mixture is stirred for 4 hours. 50 ml of water are added to the mixture under ice-cooling. The mixture is stirred at room temperature for 10 minutes. The reaction mixture is extracted with diethyl ether, the extract is washed with water and dried. The solvent is removed by evaporation under reduced pressure. 29.5 g of (4S)-2,2-dimethyl-4-tosyloxymethyl-1,3-dioxolane are obtained as pale brown oil.

$IR_{Max}^{Liquid}$ (cm$^{-1}$): 1365, 1260, 1210; Mass (m/z): 276 (M$^+$-15), 155,101, 91 (base), 43.

(2) A mixture of 9.51 g of the product obtained in the paragraph (1), 5.25 g of 6-(cyclopropylmethoxy)naphthylamine, 5.54 g of sodium iodide, 6.2 g of sodium bicarbonate and 42 ml of hexamethylphosphoric triamide is stirred at 120° C. for 11 hours. The reaction mixture is poured into water and extracted with ethyl acetate. The extract is washed with water, dried and evaporated. The residue is purified by silica gel column chromatography [solvent: ethyl acetate - hexane (1:5)]and recrystallized from ethyl acetate - hexane. 5.88 g of (4R)-4-[6-(cyclopropylmethoxy)-2 -naphthylaminomethyl]-2,2-dimethyl-1,3-dioxolane are obtained as pale yellow scales.

m.p. 108.5°-109.0° C.;

$[\alpha]_D^{20}$-12.9° (c=1.089, chloroform).

(3) A mixture of 8.09 g of the product obtained in the paragraph (2), 35 ml of 1N-hydrochloric acid and 80 ml of tetrahydrofuran is stirred at 60° C. for 2 hours. The reaction mixture is condensed under reduced pressure. The residue is basified with aqueous sodium bicarbonate solution and extracted with ethyl acetate. The extract is washed with water, dried and evaporated under reduced pressure to remove the solvent. The residue is recrystallized from ethyl acetate - hexane. 6.93 g of (2R)-3-(6-cyclopropylmethoxy-2-naphthylamino)-1,2-propandiol are obtained as pale brown scales.

m.p. 138.0°-138.5° C.

$[\alpha]_D^{20}$ +8.0° (c=0.898, tetrahydrofuran).

(4) A mixture of 1.36 g of the product obtained in the paragraph (3), 670mg of diethyl carbonate, one ml of toluene and 50 mg of sodium methoxide is stirred at 150° C. for one hour. The reaction mixture is evaporated under reduced pressure to remove the solvent. One drop of acetic acid is added to the residue. The residue is purified by silica gel column chromatography [solvent; chloroform - ethyl acetate (1:1 to 1:3)]and recrystallized from ethyl acetate - hexane. 1.06 g of (5R)-3-(6-cyclopropylmethoxy- 2-naphthyl)-5-hydoroxymethyl-2-oxazolidone are obtained as colorless needles m.p. 181.5°-182.5° C.;

$[\alpha]_D^{20}$-61.4° (c=1.031, chloroform).

EXAMPLE 12

A mixture of 626mg of (5R)-3-(6-cyclopropylmethoxy-2-naphthyl)-5-hydroxymethyl-2-oxazolidone, 114 mg of sodium hydride (63% dispersion in oil) and 5 ml of dimethylformamide is stirred at room teperature for 10 minutes. 350 mg of methyl iodide are added to the mixture, and the mixture is stirred at room temperature for 2 hours. 0.1 ml of acetic acid is added to the reaction mixture. The mixture is poured into water and extracted with ethyl acetate, and the extract is washed with water, dried and evaporated under reduced pressure to remove the solvent. The residue is purified by silica gel column chromatography [solvent: chloroform - ethyl acetate (2:1)] and recrystallized from ethyl acetate - hexane. 501 mg of (5R)-3-(6-cyclopropylmethoxy-2-naphthyl )-5-methoxymethyl-2-oxazolidone are obtained as colorless scales.

m.p. 119.0°-119.5° C.;

$[\alpha]_D^{20}$-54.2° (c=1.136, chloroform).

EXAMPLE 13

6.99 g of 5-methoxymethyl-3-(7-nitro-2-naphthyl )-2-oxazolidone are suspended in 140 ml of acetic acid, and 2.1 g of 10% palladium - carbon are added thereto. The mixture is subjected to catalytic hydrogenation under atmospheric pressure at room temperature. The reaction mixture is filtered with celite and the filtrate is evaporated under reduced pressure. The residue is extracted with ethyl acetate and the extract is washed, dried and condensed. The residue is purified by silica gel column chromatography [solvent: ethyl acetate - hexane (2:1 to 3:1)], and residue is recrystallized from ethyl acetate - isopropyl ether to give 4.96 g of 3-(7-amino-2-naphthyl)-5-methoxymethyl-2-oxazolidone.

m.p. 98°-99° C.

EXAMPLES 14 and 15

A solution of 0.97 g of sodium nitrite is 6 ml of water is added dropwise at 0° to 5° C. to a mixture of 3.47 g of 3-(7-amino-2-naphthyl)-5-methoxymethyl-2-oxazolidone, 6 ml of water and 3.3 ml of conc. hydrochloric acid. After the mixture is stirred for a few minutes. 100 ml of methanol are added thereto. The mixture is stirred at room temperature for 7 hours and then allowed to stand in a refrigerator overnight. The reaction mixture is extracted with ethyl acetate and the extract is washed and dried. The aqueous layer is further extracted with chloroform and the extract is dried. The residue (1.88 g) is purified by silica gel column chromatography [solvent: ethyl acetate - hexane (1:1)]. 5-methoxymethyl-3-(7-methoxy-2-naphthyl)-2-oxazolidone [Example 14) m.p. 95.5°-96.5° C. (recrystallized from ethyl acetate - hexane)] and 3-(7-hydroxy-2-naphthyl)-5- methoxymethyl-2-oxazolidone [Example 15, m.p. 155°-157° C. (recrystallized from ethyl acetate - hexane)]are obtained.

EXAMPLE 16

1.0 ml of thionyl chloride is added to a suspension of 3.0 g of sodium 6-(5-methoxymethyl-2-oxazolidone-3- yl)-2-naphthylsulfonate in 24 ml of dimethylformamide under ice-cooling. The mixture is stirred at room temperature for one hour. After ice-cooling, the mixture is poured into ice-water and extracted with ethyl acetate. The extract is washed, dried and evaporated under reduced pressure to remove the solvent to give 2.9 g of pale brown foam.

The foam is dissolved in 50 ml of tetrahydrofuran and 10 ml of conc. aqueous ammonium hydroxide solution are added thereto. The mixture is stirred at room temperature for 2 hours. 200 ml of water are added to the mixture. The mixture is stirred for a minute and allowed to stand overnight at room temperature. Crystalline precipitates are collected and recrystallized from ethanol. 1.97 g of 3-(6-aminosulfonyl-2-naphthyl)-5-methoxymethyl-2-oxazolidone are obtained as colorless powder.

m.p. 166°–168° C.

EXAMPLE 17

18.9 g of 3-(6-benzyloxy-2-naphthyl)-5-methoxymethyl-2-oxazolidone is dissolved in 700 ml of tetrahydrofuran and 10.0 g of 10% of palladium - carbon are added thereto. The mixture is subjected to catalytic hydrogenation under atmospheric pressure at room temperature for 10 hours. The catalyst is filtered off, and the filtrate is evaporated under reduced pressure to remove the solvent. The residue is recrystallized from ethanol - tetrahydrofuran - isopropyl ether. 11.2 g of 3-(6-hydroxy-2-naphthyl)-5-methoxymethyl-2-oxazolidone are obtained as colorless needles.

m.p. 192°–193° C.

EXAMPLE 18

30.6 g of 3-(6-benzyloxy-2-naphthyl)-5-tert.-butoxymethyl-2-oxazolidone are treated in the same manner as described in Example 17. 22.7 g of 3-(6-hydroxy-2-naphthyl)-5-tert.-buthoxymethyl-2-oxazolidone are obtained as colorless crystals. m.p. 177°–178° C. (tetrahydrofuran - isopropyl ether - hexane).

EXAMPLE 19

5.06 g of potassium carbonate and 2 ml of ethyl iodide are added to a solution of 2.0 g of 3-(6-hydroxy-2-naphthyl)-5-methoxymethyl-2-oxazolidone in 25 ml of dimethyl formamide. The mixture is stirred for 4 hours at room temperature. The reaction mixture is diluted with ethyl acetate, washed with water and dried. The residue is recrystallized from ethyl acetate - isopropyl ether. 1.89 g of 3-(6-ethoxy-2-naphthyl)-5-methoxymethyl-2-oxazolidone are obtained as colorless plates. m.p. 129.5°–130.5° C.

EXAMPLES 20 to 46

The corresponding starting compounds are treated in the same manner as described in Example 19 to give a compounds shown in Table 6.

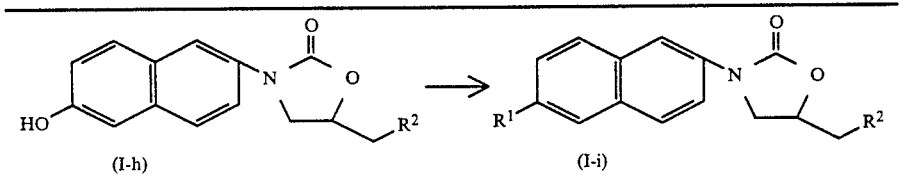

| Ex. No. | R$^1$ | R$^2$ | Melting Point |
|---|---|---|---|
| 20 | —O(CH$_2$)$_2$CH$_3$ | —OCH$_3$ | 94.5–95.5° C. (ethyl acetate - hexane) |
| 21 | —OCH(CH$_3$)$_2$ | | 111.5–116° C. (ethyl acetate - hexane) |
| 22 | —O(CH$_2$)$_3$CH$_3$ | | 80.5–81° C. (ethyl acetate - hexane) |
| 23 | —OCH(CH$_3$)CH$_2$CH$_3$ | | 79–80° C. (ethyl acetate - hexane) |
| 24 | —OCH$_2$CH(CH$_3$)$_2$ | | 114–114.5° C. (ethyl acetate - hexane) |
| 25 | —O(CH$_2$)$_4$CH$_3$ | | 82–83° C. (ethyl acetate - hexane) |
| 26 | —O(CH$_2$)$_2$CH(CH$_3$)$_2$ | | 88–89° C. (ethyl acetate - hexane) |
| 27 | —OCH$_2$—△ | | 120–121° C. (ethyl acetate - isopropyl ether) |
| 28 | —OCH$_2$-(tetrahydrofuranyl) | —OCH$_3$ | 113–125° C. (ethyl acetate - isopropyl ether) |
| 29 | —O(CH$_2$)$_2$OH | | 120–121° C. (ethyl acetate - isopropyl ether) |
| 30 | —O(CH$_2$)$_3$OH | | 87.5–88.5° C. (ethyl acetate - hexane) |
| 31 | —O(CH$_2$)$_2$OCH$_3$ | | 102–103° C. (ethyl acetate - hexane) |
| 32 | —O(CH$_2$)$_2$OC$_2$H$_5$ | | 82–84° C. (ethyl acetate - hexane) |
| 33 | —OCH$_2$CN | | 97–98° C. (ethyl acetate - hexane) |
| 34 | —O(CH$_2$)$_3$CN | | 84.5–86° C. |

-continued

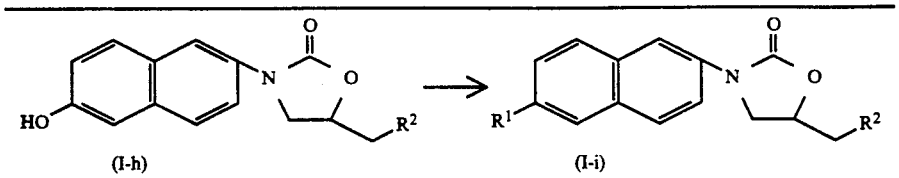

(I-h) → (I-i)

| Ex. No. | R¹ | R² | Melting Point |
|---|---|---|---|
| 35 | —O(CH₂)₂N(CH₃)₂ | | (ethyl acetate - hexane) 207-207.5° C. Hydrochloride (methanol - diethyl ether) |
| 36 | —OCH₂CONH₂ | | 176.5-177.5° C. (ethyl acetate - hexane) |
| 37 | —OCH(CH₃)CO₂CH₃ | | 91-95° C. (ethyl acetate - hexane) |
| 38 | —OCH₂CH=CH₂ | | 108.5-109.5° C. (ethyl acetate - hexane) |
| 39 | —O(CH₂)₂CH=CH₂ | —OCH₃ | 90-92° C. (ethyl acetate hexane) |
| 40 | —OCH₂CH=C(CH₃)₂ | | 105.5-107° C. (ethyl acetate - hexane) |
| 41 | —OCH₂C≡CH | | 99.5-100.5° C. (ethyl acetate - hexane) |
| 42 | —O(CH₂)₂OCOCH₃ | | 89-92° C. (ethyl acetate - hexane) |
| 43 | —O(CH₂)₂SCH₃ | | 81-84° C. (ethyl acetate - hexane) |
| 44 | —OCON(CH₃)₂ | | 107-108° C. (ethyl acetate - hexane) |
| 45 | —O(CH₂)₂CH₃ | —OC(CH₃)₃ | 121-122° C. (ethyl acetate - hexane) |
| 46 | —O(CH₂)₃CH₃ | | 123-123.5° C. (ethyl acetate - hexane) |

EXAMPLE 47

A mixture of 720 mg of 3-(6-hydroxy-2-naphthyl)-5-methoxymethyl-2-oxazolidone, 5 ml of acrylonitrile, 5 ml of tetrahydrofuran and 0.1 ml of methanolic 40% benzyltrimethylammonium hydroxide solution is refluxed for 2 days. The reaction mixture is condensed under reduced pressure to dryness. The residue is extracted with ethyl acetate, and the extract is washed with water, dried and condensed under reduced pressure. The residue is purified by silica gel column chromatography [solvent: chloroform - methanol (20:1)] and recrystallized from ethyl acetate - hexane. 410 mg of 3-(6-cyanoethoxy-2-naphthyl)-5-methoxymethyl-2-oxazolidone are obtained as colorless scale.
m.p. 110°-112° C.

EXAMPLES 48 to 50

The corresponding starting compounds are treated in the same manner as described in Example 47 to give the compounds shown in Table 7.

TABLE 7

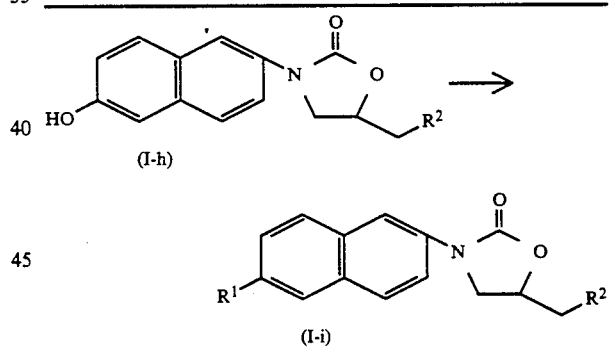

(I-h) →

(I-i)

| Ex. No. | R¹ | R² | Melting Point |
|---|---|---|---|
| 48 | —O(CH₂)₂CN | —O(CH₃)₃ | 175.5-177° C. (ethyl acetate) |
| 49 | —O(CH₂)₂CO₂CH₃ | —OCH₃ | 111-112° C. (ethyl acetate - hexane) |
| 50 | —O(CH₂)₂CO₂C₂H₅ | —OCH₃ | 91.5-93° C. (ethyl acetate - hexane) |

EXAMPLE 51

A mixture of 950 mg of 3-(6-hydroxy-2-naphthyl)-5-methoxymethyl-2-oxazolidone, 310 mg of ethyl isocyanate, 15 ml of methylene chloride, 10 ml of tetrahydrofuran and one drop of triethylamine is stirred at room temperature for 4 hours. 1.5 g of ethyl isocyanate are further added to the mixture, and the mixture is refluxed for 3 hours. The reaction mixture is condensed under reduced pressure. The residue is dissolved in ethyl acetate and washed with water treated with charcol and dried. The solvent is removed by evaporation under reduced pressure. The residue is recrystallized from ethyl acetate - isopropyl ether. 800 mg of 3-(6-ethylaminocarbonyloxy 2-naphthyl)5-methoxymethyl-2-oxazolidone are obtained as colorless prisms.

m.p. 126.5°–127.5° C.

EXAMPLE 52

A mixture of 2.0 g of 3-(6-hydroxy-2-naphthyl)-5-methoxy-methyl-2-oxazolidone and 10 ml of acetic anhydride is refluxed for one hour. The reaction mixture is evaporated to remove an excess acetic anhydride. The residue is recrystallized from ethyl acetate - isopropyl ether. 2.25 g of 3-(6-acetyloxy-2-naphthyl)-5-methoxymethyl-2-oxazolidone are obtained as colorless crystals.

m.p. 110°–112.5° C.

EXAMPLE 53

1.07 g of m-chloroperbenzoic acid are gradually added at room temperature to a mixture of 1.88 g of 5-methoxymethyl-3-[6-(methylthioethoxy)-2-naphthyl]-2-oxazolidone and 100 ml of methylene chloride. The mixture is stirred at room temperature for one hour. The reaction mixture is washed with 10% aqueous sodium hydroxide solution and water, and then dried. The solvent is removed by evaporation under reduced pressure. The residue is purified by silica gel column chromatography [solvent: chloroform - methanol (30:1)]and recrystallized from ethyl acetate - tetrahydrofuran - isopropyl ether. 1.21 g of 5-methoxymethyl-3-[6-(methylsulfinylethoxy) -2-naphthyl]-2-oxazolidone are obtained as colorless prisms.

m.p. 133°–141° C.

EXAMPLE 54

1.65 g of m-chloroperbenzoic acid are gradually added at room temperature to a mixture of 1.20 g of 5-methoxymethyl-3-[6-(methylthioethyloxy)-2-naphthyl]-2-oxazolidone and 40 ml of methylene chloride. The mixture is stirred at room temperature for 3 hours. The reaction mixture is washed with 10% aqueous sodium hydroxide solution and water and then dried. The solvent is removed by evaporation under reduced pressure. The residue is purified by silica gel column chromatography [solvent: chloroform - ethyl acetate (1:1)]and then recrystallized from ethanol - tetrahydrofuran - isopropyl ether. 0.73 g of 5-methoxymethyl-3-[6-(methylsulfonylethyloxy) -2 -naphthyl]-2-oxazolidone are obtained as colorless needles.

m.p. 128°–129° C.

EXAMPLE 55

10 ml of trifluoroacetic acid are added to 3.36 g of 3-(2-naphthyl)-5-tert.-butoxymethyl-2-oxazolidone under ice-cooling. The mixture is stirred at room temperature for one hour. The reaction mixture is evaporated under reduced pressure to remove trifluoroacetic acid. The residue is recrystallized from ethanol - dimethylformamide - isopropyl ether. 2.16 g of 5-hydroxymethyl-3-(2-naphthyl)-2-oxazolidone are obtained as colorless crystals.

m.p. 174°–174.5° C.

EXAMPLES 56 to 58

The corresponding starting compounds are treated in the same manner as described in Example 55 to give compounds shown in Table 8.

TABLE 8

| Ex. No. | R$^1$ | Melting Point |
|---|---|---|
| 56 | —O(CH$_2$)$_2$CH$_3$ | 149–150° C. (ethyl acetate - isopropyl ether) |
| 57 | —O(CH$_2$)$_3$CH$_3$ | 127–130° C. (ethyl acetate - isopropyl ether) |
| 58 | —O(CH$_2$)$_2$CN | 122–125° C. (ethyl acetate - isopropyl ether) |

EXAMPLE 59

A mixture of 8.5 g of methylsulfonyl chloride and 120 ml of methylene chloride is added dropwise to a suspension of 12.0 g of 5-hydroxymethyl-3-(2-naphthyl)-2-oxazolidone, 240 ml of methylene chloride and 10.0 g of triethylamine under ice-cooling. The mixture is stirred at room temperature for 3 hours. A mixture of 1.0 g of methylsulfonyl chloride and 50 ml of tetrahydrofuran is added dropwise to the mixture, and the mixture is stirred at room temperature for 2 hours. The reaction mixture is washed with water. The extract is dried, and then evaporated under reduced pressure to remove the solvent. The residue is recrystallized from isopropyl ether. 14.7 g of 5-methylsulfonyloxymethyl-3-(2-naphthyl)-2-oxazolidone are obtained as colorless crystals.

m.p. 169°–172° C.

EXAMPLE 60

A mixture of 3.0 g of 5-methylsulfonyloxymethyl-3-(2-naphthyl)-2-oxazolidone, 120 ml of an aqueous 40% methylamine solution, 100 ml of tetrahydrofuran and 50 ml of dimethylformamide is stirred at room temperature in a sealed tube for 2 days. The reaction mixture is evaporated under reduced pressure to remove the excess methylamine and tetrahydrofuran. The mixture is extracted with ethyl acetate, and the extract is washed with water, dried evaporatedunder reduced pressure to remove the solvent. The residue is purified by silica gel column chromatography [solvent: chloroform - methanol (20:1)] and recrystallized from ethyl acetate - hexane. 1.12 g of 5-methylaminomethyl-3-(2-naphthyl)-2-oxazolidone are obtained as colorless crystals.

m.p. 76.5°–78.0° C.

EXAMPLE 61

A mixture of 11.6 g of 5-methylsulfonyloxymethyl-3-(2-naphthyl)-2-oxazolidone, 230 ml of dimethylformamide, 4.84 g of sodium azide and 23 ml of water is stirred at 80° C. for 9 hours. The reaction mixture is poured into water, extracted with ethyl acetate, and the extract is washed with water, dried and evaporated under reduced pressure to remove the solovent. The residue is recrystallized from ethyl acetate - hexane. 8.62 g of 3-(2-naphthyl)-5-triazomethyl-2-oxazolidone are obtained as colorless crystals.

m.p. 115.0°–116.5° C.

EXAMPLE 62

8.35 g of 3-(2-naphthyl)-5-triazomethyl-2-oxazolidone are dissolved in a mixture of 100 ml of tetrahydrofuran and 100 ml of acetic acid. 2.0 g of 10% palladium - carbon are added to the solution. The mixture is subjected to catalytic hydrogenation at room temperature under atmospheric pressure. After the palladium - carbon is removed, the filtrate is evaporated under reduced pressure to remove the solvent. The residue is basified with an aqueous sodium bicarbonate solution. Crystalline precipitates are collected by filtration, and washed with water. The mixture is purified by silica gel column chromatography [solvent: chloroform - methanol (40:1 to 8:1)] and recrystallized from ethanol - isopropyl ether - hexane. 4.90 g of 5-aminomethyl-3-(2-naphthyl)-2-oxazolidone are obtained as colorless crystals.

m.p. 112°–114° C.

EXAMPLE 63

A mixture of 1.8 g of 5-aminomethyl-3-(2-naphthyl)-2-oxazolidone, 36 ml of chloroform, 1.5 ml of acetic anhydride and 1.5 ml of pyridine is stirred at room temperature for one hour. The reaction mixture is washed with water, dried and evaporated under reduced pressure to remove the solvent. The residue is recrystallized from ethyl acetate - isopropyl ether. 1.56 g of 5-acetylaminomethyl-3-(2-naphthyl)-2-oxazolidone are obtained as colorless crystals.

m.p. 152°–154° C.

EXAMPLE 64

(1) A mixture of 2.0 g of 3-(6-benzyloxy-2-naphthyl)-5-methoxymethyl-2-oxazolidone, 20 ml of ethanol, 4 ml of water and 1.08 g of potassium hydroxide is stirred at 100° C. for one hour. The reaction mixture is evaporated under reduced pressure to remove the ethanol. The residue is extracted with ethyl acetate, and the extract is washed with water, dried and evaporated under reduced pressure to remove the solvent. The residue is recrystallized from ethyl acetate - hexane to give 1.64 g of N-(3-methoxy-2-hydroxypropyl)-6-benzyloxy-2-naphthylamine as colorless needles.

m.p. 103°–104° C.

(2) A mixture of 3.53 g of ethyl chloroformate and 5 ml of methylene chloride is added dropwise to a mixture of 10.0 g of the product obtained in the the paragraph (1), 70 ml of methylene chloride, 70 ml of water and 4.98 g of sodium bicarbonate under ice-cooling. The mixture is stirred at room temperature for 1.5 hours. A mixture of 0.35 g of ethyl chloroformate and 2 ml of methylene chloride is added to the mixture, and the mixture is further stirred at room temperature for 4 hours. Organic layer is separated from the reaction mixture. The aqueous layer is extracted with methylene chloride and conbined with the organic layer. The conbined solution is dried and then evaporated under reduced pressure to remove the solvent. The residue is purified by silica gel column chromatography [solvent: ethyl acetate - hexane (1:1)]. 12.66 g of N-ethoxycarbonyl-N-(3-methoxy-2-hydroxypropyl)-6-benzyloxy-2-naphthylamine are obtained as colorless oil.

$IR_{Max}^{Neat}$ (cm$^{-1}$): 3450 (br), 1700, 1605; Mass (m/z): 409 (M+), 318, 91 (base).

(3) A mixture of 4.68 g of pyridine and 10 ml of tetrahydrofuran is added dropwise to a mixture of 12.12 g of the product obtained in the paragraph (2), 120 ml of tetrahydrofuran and 11.5 g of (2S)-1-(2-naphthylsulfonyl)pyrrolidin-2-carbonyl chloride under ice-cooling. The mixture is stirred at room temperature for 3.5 hours. The reaction mixture is diluted with 500 ml of ethyl acetate, washed with 5% hydrochloric acid and water, dried and evaporated to remove the solvent. The residue is purified by silica gel column chromatography [solvent: ethyl acetate - hexane (2:3)]. 9.48 g of N-ethoxycarbonyl-N-{(2R)-3-methoxy-2-[(2S)-1-(2-naphthylsulfonyl)pyrrolidin-2-carbonyloxy]propyl}-6-benzyloxy-2 -naphthylamine (Product A) and 9.28 g of N-ethoxycarbonyl-N-{(2S)-3-methoxy-2-[(2S)- 1-(2-naphthylsulfonyl) pyrrolidin-2-carbonyloxy]-propyl}-6-benzyloxy-2-naphthylamine (Product B) are obtained as colorless oils.

Product A:

$IR_{Max}^{Chloroform}$ (cm$^{-1}$): 1750 (br), 1695 (br), 1605; $[\alpha]_D^{20}$ −35.50° (c=0.569, chloroform).

Product B:

$IR_{Max}^{Chloroform}$ (cm$^{-1}$): 1750 (br), 1695, 1605; $[\alpha]_D^{20}$ −56.42° (c=0.677. chloroform).

(4) A mixture of 8.95 g of Product A obtained in paragrapyh (3), 2.57 g of sodium hydroxide. 100 ml of ethanol and 20 ml of water is stirred at 100° C. for one hour. The reaction mixture is evaporated under reduced pressure to remove the solvent, and water is added to the residue. The mixture is extracted with ethyl acetate. The extract is washed with water, dried and condenced. Hexane is added to the residue, and crystalline precipitates are collected by filtration. 3.76 g of N-[(2R)-3-methoxy-2-hydroxypropyl]-6-benzyloxy-2-naphthylamine are obtained as colorless crystals.

m.p. 105°–106° C.; $[\alpha]_D^{20}$ −8.2° (c=0.533, chloroform).

(5) A mixture of 3.65 g of the product obtained in the paragraph (4), 70 ml of dry methylene chloride, 3.51 g of carbonyldiimidazol and 0.14 g of diisopropylethylamine is stirred at room temperature for 2 hours. The reaction mixture is washed with 5% hydrochloric acid. The aqueous layer is extracted with ethyl acetate, and the extract is conbined with the organic layer. The mixture is dried and evaporated under reduced pressure to remove tile solvent. The residue is recrystallized from ethyl acetate to give 3.60 g of (5R)-3-(6-benzyloxy-2-naphthyl)-5-methoxymethyl-2-oxazolidone as colorless scales.

m.p. 150°–150.5° C.; $[\alpha]_D^{20}$ −51.1° (c=0.305, chloroform).

EXAMPLE 65

(1) 9.2 g of N-ethoxycarbonyl-N-{(2S)-3-methoxy-2-[(2S)-1-(2-naphthysulfonyl)-2-pyrrolidinylcarbonyloxy]propyl}-6-benzyloxy-2-naphthylamine are treated in the same manner as described in Example 64-(4). 3.76 g of N-[(2S)-3-methoxy-2-hydroxypropyl]-6-benzyloxy-2-naphthylamine are obtained as colorless needles.

m.p. 105°–106° C.;

$[\alpha]_D^{20}$ +7.90° (c=0.354, chloroform), (2) 3.62 g of the product obtained in the paragraph (1) are treated in the same manner as described in Example 64-(5). 3.55 g of (5S)-3-(6-benzyloxy-2-naphthy)-5- methoxymethyl-2-oxazolidone as colorless needles.

m.p. 149.5°-150.5° C.; $[\alpha]_D^{20}$ +49.9° (c=0.305, chloroform).

EXAMPLE 66

A mixture of 16.9 g of (5R)-3-(6-benzyloxy-2-naphthyl)-5-methoxymethyl-2-oxazolidone, 8.50 g of 10% palladium-carbon and 400 ml of tetrahydrofuran are hydrogenated at 45° to 50° C. for 2 hours under atmospheric pressure. Insoluble materials are filtered off. The filtrate is evaporated under reduced pressure to remove the solvent. The residue is recrystallized from tetrahydrofuran - isopropyl ether. 11.5 g of (5R)-3-(6-hydroxy-2-naphthyl)-5-methoxymethyl-2-oxazolidone are obtained as colorless prisms.

m.p. 190°-191° C.; $[\alpha]_D^{20}$ −74.0° (c=0.396, tetrahydrofuran).

EXAMPLE 67

15.0 g of (5S)-3-(6-benzyloxy-2-naphthyl)-5-methoxymethyl-2-oxazolidone are treated in the same manner as described in Example 66. 10.3 g of (5S)-3-(6-hydroxy-2-naphthyl)-5-methoxymethyl-2-oxazolidone are obtained as colorless prisms.

m.p. 190°-191° C.; $[\alpha]_D^{20}$ +77.1° (c=0.358, tetrahydrofuran).

EXAMPLE 68

A mixture of 2.38 g of (5R)-3-(6-hydroxy-2-naphthyl)-5-methoxymethyl-2-oxazolidone, 1.83 g of cyclopropylmethyl bromide, 3.55 g of potassium carbonate and 30 ml of dimethylformamide is stirred at 50° C. for 7 hours. The reaction mixture is poured into water, extracted with ethyl acetate. The extract is washed with water, dried and evaporated under reduced pressure to remove the solvent. The residue is purified by silica gel column chromatography [solvent: ethyl acetate -chloroform (1:10)] and recrystallized from ethyl acetate - hexane. 2.51 g of (5R)-3-(6-cyclopropylmethoxy-2-naphthyl)-5-methoxymethyl-2-oxazolidone are obtained as colorless scales.

m.p. 120.5°-121° C.; $[\alpha]_D^{20}$ −54.4° (c=1.08, chloroform).

EXAMPLE 69

3.69 g of (5S)-3-(6-hydroxy-2-naphthyl)-5-methoxymethyl-2-oxazolidone and 2.84 g of cycropropylmethyl bromide are treated in the same manner as described in Example 68. 4.07 g of (5S)-3-(6-cyclopropylmethoxy-2-naphthyl)-5- methoxymethyl-2-oxazolidone as colorless scales.

m.p. 119°-119.5° C.; $[\alpha]_D^{20}$ +54.4° (c=1.05, chloroform).

What is claimed is:

1. A naphthyloxazolidone compound of the formula:

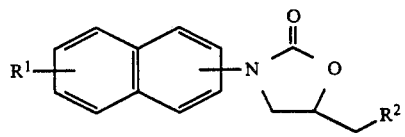

wherein $R^1$ is a hydrogen atom, a hydroxy group, a lower alkenyloxy group, a lower alkanoyloxy group or a lower alkoxy group which is unsubstituted or has a substituent selected from the group consisting of a cycloalkyl group of 3 to 6 carbon atoms, a hydroxy group, a lower alkoxy group, a cyano group, a lower alkanoyloxy group, and a lower alkylthio group; and $R^2$ is a hydroxy group or a lower alkoxy group; or a pharmaceutically acceptable salt thereof.

2. A compound in accordance with claim 1, wherein $R^1$ is a lower alkenyloxy group, a lower alkanoyloxy group, or a lower alkoxy group which is unsubstituted or has a substituent selected from the group consisting of a cyclopropyl group, a hydroxy group, and a cyano group.

3. A compound in accordance with claim 2, wherein $R^2$ is a lower alkoxy group.

4. A compound in accordance with claim 3, wherein $R^1$ is a lower alkoxy group which is unsubstituted or has a substituent selected from the group consisting of a cyclopropyl group and a cyano group.

5. A compound in accordance with claim 1, wherein $R^2$ is a lower alkoxy group.

6. A compound in accordance with claim 1, wherein $R^1$ is at the 6-position of the naphthalene ring and the 5-substituted-2-oxazolidon-3-yl group is at the 2-position of the naphthalene ring.

7. A compound in accordance with claim 2, wherein $R^1$ is at the 6-position of the naphthalene ring and the 5-substituted-2-oxazolidon-3-yl group is at the 2-position of the naphthalene ring.

8. A compound in accordance with claim 3 wherein $R^1$ is at the 6-position of the naphthalene ring and the 5-substituted-2-oxazolidon-3-yl group is at the 2-position of the naphthalene ring.

9. A compound in accordance with claim 4, wherein $R^1$ is at the 6-position of the naphthalene ring and the 5-substituted-2-oxazolidon-3-yl group is at the 2-position of the naphthalene ring.

10. A pharmaceutical composition which comprises a pharmaceutically effective amount of the compound claimed in claim 1 and a pharmaceutically acceptable carrier therefor.

11. A method for treatment or prophylaxis of depressive conditions in a warm-blood animal which comprises administering to said warm-blood animal a pharmaceutically effective amount of the compound claimed in claim 1.

* * * * *